United States Patent [19]

Eisenhuth et al.

[11] Patent Number: 4,459,424
[45] Date of Patent: Jul. 10, 1984

[54] PROCESS FOR THE PREPARATION OF THIURAM DISULFIDES

[75] Inventors: Ludwig Eisenhuth, Elsenfeld; Hans G. Zengel, Kleinwallstadt; Manfred Bergfeld, Erlenbach, all of Fed. Rep. of Germany

[73] Assignee: Akzona Incorporated, Asheville, N.C.

[21] Appl. No.: 349,352

[22] Filed: Feb. 16, 1982

[30] Foreign Application Priority Data

Feb. 16, 1981 [DE] Fed. Rep. of Germany ....... 3105622

[51] Int. Cl.$^3$ ............................................. C07C 155/10
[52] U.S. Cl. ..................... 564/76; 544/160; 546/245; 548/523
[58] Field of Search ......................................... 564/76

[56] References Cited

U.S. PATENT DOCUMENTS

| 3,116,328 | 12/1963 | Cox et al. | 564/76 |
| 3,116,329 | 12/1963 | Hayes et al. | 564/76 |
| 3,248,400 | 4/1966 | Flieg et al. | 564/76 X |
| 3,737,431 | 6/1973 | Campbell et al. | 564/76 X |
| 3,992,448 | 11/1976 | Parkinson | 564/76 |
| 4,120,764 | 10/1978 | Torii et al. | 564/76 X |
| 4,144,272 | 3/1979 | Bergomi et al. | 564/76 |

OTHER PUBLICATIONS

Issoire et al., CA 55: 1641a, (1961).
Rothstein et al., CA 49: 14646i, (1955).

Primary Examiner—Thomas A. Waltz
Attorney, Agent, or Firm—Francis W. Young; Daniel N. Christus; Jack H. Hall

[57] ABSTRACT

A process for the preparation of thiuram disulfides substituted with aliphatic cycloaliphatic, araliphatic, or aromatic hydrocarbon radicals, said process comprising reacting a suitably substituted secondary amine having a $pK_a \geq 8$ with carbon disulfide in a solvent and in the presence of oxygen or oxygen-containing gas, a solvent, and a metalliferous catalyst, at a temperature of between 0° C. and 200° C.

9 Claims, No Drawings

PROCESS FOR THE PREPARATION OF THIURAM DISULFIDES

BACKGROUND OF THE INVENTION

The invention refers to a process for the preparation of thiuram disulfides substituted with aliphatic, araliphatic and/or cycloaliphatic hydrocarbons from suitably substituted secondary amines and carbon disulfide in the presence of oxygen and a metalliferous catalyst.

Making use of known processes, thiuram disulfides can be obtained by the oxidative dimerization of salts of substituted dithiocarbamic acids. Hydrogen peroxide, nitrogen dioxide, chlorine, bromine, iodine, ozone, oxygen, sodium nitrite, sodium hypochlorite, sulfur chlorides, potassium perbromate, selenic acid, or ammonium persulfate are used as oxidant. Tetramethyl thiuram disulfide, one of the most important representatives of this category of compounds, is made on an industrial scale by means of a two-stage process. In the first stage, dimethylamine and carbon disulfide in aqueous sodium hydroxide are reacted to form sodium-N,N-dimethyl dithiocarbamate. In the second stage the dithiocarbamate is oxidized with hydrogen peroxide in the presence of sulfuric acid (Bios 1150, Fiat 1018), with chlorine (U.S. Pat. Nos. 2,751,514 and 2,751,416), or electrolytically (German patent application disclosure Nos. 28 02 260 and 28 03 591).

In the process of German Pat. No. 12 26 564, a secondary alkyl-, aryl- or alkylarylamine is reacted with carbon disulfide in an aqueous or non-aqueous medium and in the presence of an oxygen-containing gas and a metal catalyst to form substituted thiuram disulfide. A sulfonated or carboxylated metal phthalocyanine of the 8th group of the periodic system, as for example cobalt phthalocyanine, is used as catalyst. In this process, the yield is relatively low; at best, it is about 25% of theoretical. When aromatic amines such as diphenylamine are used, the process of German Pat. No. 12 26 564 does not result in the formation of thiuram disulfide. In addition, the preparation and industrial use of the cobalt catalyst are problematical.

The use of a metalliferous catalyst in the oxidation of alkali salts of substituted dithiocarbamic acids with oxygen is also known. According to the process of German published application No. 11 65 011, the oxidation is carried out in an aqueous solution of a sulfonated or carboxylated Group VIII metal phthalocyanine at a pH of about 7 to 12. However, materials used in this process add to its expense and form unusable by-products. Lye is needed for the preparation of the dithiocarbamates and hydrochloric acid is required for pH adjustment, and these form unusable sodium chloride. Further, the industrial preparation and application of these Group VIII metalliferous catalysts is problematical.

The use of an ammonium salt of dithiocarbamic acid, instead of the alkali salts, is also already known. In the process of German patent application disclosure No. 25 27 898, ammoniumdimethyldithiocarbamate is oxidized by means of hydrogen peroxide in an aqueous solution of sulfuric acid at a pH of from 5 to 7 to yield a suspension of solid tetramethyl thiuram disulfide in an aqueous ammonium sulfate solution. After the solid tetramethyl thiuram disulfide has been filtered off the resulting filtrate must be concentrated down to the solubility limit of the ammonium sulfate, resulting in its precipitation. The ammonium sulfate could be used as a fertilizer, but only if the adhering dithiocarbamate is removed. This makes the ammonium sulfate an undesirable byproduct.

Surprisingly, it has now been found that upon oxidation of secondary amines with a $pK_a \geq 8$ and carbon disulfide with oxygen to form thiuram disulfides, the yield and selectivity can increase considerably when certain metals or derivatives are selected as catalyst.

An object of the invention is a process for the preparation of a thiuram disulfide substituted with aliphatic, araliphatic, and/or cycloaliphatic hydrocarbon radicals by reacting a suitably substituted secondary amine with carbon disulfide in a solvent and in the presence of oxygen or a gas containing oxygen and a metalliferous catalyst. The reaction is carried out with a secondary amine with a $pK_a$ value of $\geq 8$, and at temperatures from 0° to 200° C., and comprises reacting carbon disulfide and the secondary amine in a molar ratio of 1.0 to 1.2:1 in the presence of oxygen or a gas containing oxygen and the metalliferous catalyst. A second embodiment comprises reacting carbon disulfide and the secondary amine in a molar ratio of 0.9 to 1.1:2.0 to 2.2, and then reacting the resulting reaction product with 1.0 to 1.2 moles of carbon disulfide per mole of carbon disulfide originally reacted, in the presence of oxygen or a gas containing oxygen and the metalliferous catalyst. A still further embodiment comprises reacting carbon disulfide and the secondary amine in a molar ratio of 0.9 to 1.1:2.0 to 2.2, reacting the formed dithiocarbamate with carbon disulfide in a molar ratio of 1.0:1.0 to 1.2 in the presence of oxygen or a gas containing oxygen and the metalliferous catalyst, wherein said catalyst is selected from the group of metals including cerium, manganese, copper, molybdenum, vanadium, a derivative of the said metals, or a mixture of said metals or derivatives.

The process pursuant to the invention is suitable for the preparation of many different substituted thiuram disulfides. When only a single secondary amine is used as reactant, one obtains a thiuram disulfide carrying the same substituents on both nitrogen atoms. In the case of a symmetrically substituted secondary amine, one therefore obtains a thiuram disulfide with four identical substituents. When two different secondary amines are used as reactants, one can, depending upon the process conditions such as differences in the basicity of the amines or molar ratios, obtain thiuram disulfides with two different substituted nitrogen atoms. Varying quantities of the two symmetrically substituted thiuram disulfides can thereby be formed as by-products.

The metalliferous catalysts used as cerium, manganese, copper, molybdenum or vanadium in elemental form, or as salts, complexes, or in the form of their organic compounds. Among these metals or their derivatives, copper, manganese and cerium have a greater catalytic effectiveness compared with molybdenum and vanadium, but the two latter metals and their derivatives are also excellent oxidation catalysts.

Elemental copper is preferably used as copper powder. Suitable copper compounds include all mono- or divalent inorganic, organic, simple, or complex copper salts. Examples of suitable monovalent copper salts are copper(I) chloride, bromide and iodide, addition compounds of these copper(I) halides with carbon monoxide, complex copper(I) salts, such as the alkali chlorocuprates, complex ammoniacates of copper(I) cyanide, such as cyanocuprates, e.g. potassium tricyanocuprate(I), double salts with copper(I) thiocyanate, copper(I) acetate, copper(I) sulfide and complex double sulfides or copper(I) sulfide and alkali polysulfides. Examples of suitable copper(II) salts are copper(II) chloride, bromide, sulfide, nitrite, thiocyanate, or cyanide, Cu(II) salts of carboxylic acids, such as copper(II) acetate, copper dithiocarbamate, as well as the complex ammoniacates of copper(II) salts. Copper(I) oxide is also very well suited as catalyst.

Suitable manganese-containing catalysts include manganese powder, manganese dioxide, potassium permanganate, manganese acetate, and the manganese dithiocarbamates as well as the other manganese derivatives corresponding to the above-mentioned copper compounds.

Suitable cerium catalysts include metallic cerium, cerium dioxide, cerium(II) chloride, cerium chloride, cerium chlorocomplex salts, cerium nitrate, cerium nitrato salts, cerium sulfate, cerium carbonate, cerium oxalate and the cerium sulfides.

Examples of suitable vanadium catalysts are the vanadium oxides, chlorides and sulfates, as well as the known double and complex salts.

Finally, the suitable molybdenum catalysts include molybdenum oxides, chlorides, sulfides and fluorides, the molybdates, and the known complex acido salts. Mixtures of several of the above-mentioned catalysts may also be used.

The required quantity of metalliferous catalyst is surprisingly small. Preferably, it is within a range of from 0.01 to 5 millimoles per mole of secondary amine. Smaller quantities of catalyst may also be used, but reaction times will then be extended. Larger quantities of catalysts should be avoided because of the danger that the catalyst would precipitate and contaminate the reaction product.

The following are examples of aliphatic secondary amines suitable for the process pursuant to the invention: dimethylamine, diethylamine, dipropylamine, di-isopropylamine, dibutylamine, di-sec-butylamine, di-tert.-butylamine, di-(2-methylpropyl)-amine, dipentylamine, di-(1-methylbutyl)-amine, di-(2-methylbutyl)-amine, di-(3-methyl-butyl)-amine, di-(1,1-methylpropyl)-amine, di-(2,2-dimethyl-propyl)-amine, di(1,2-dimethylpropyl)-amine, dihexyl-amine, di-(1-methylpentyl)-amine, di-(2-methylpentyl)-amine, di(3-methylpentyl)-amine, di-(3-ethylpentyl)-amine, di-(1,1-dimethyl-butyl)-amine, di-(2,2-dimethylbutyl)-amine, di(3,3-dimethylbutyl)-amine, di-(2,3-dimethybutyl) amine, di-(1-ethylbutyl)amine, di-(2-ethybutyl)-amine, diheptylamine, di-(1-methylhexyl-amine, di-(2-methylhexyl)-amine, di-(3-methylhexyl)-amine, di-(4-methylhexyl)-amine, di-(5-methylhexyl)-amine, di-(1-ethylpentyl) amine, di-(2-ethylpentyl)-amine, di-(3-ethylpentyl)-amine, dioctylamine, di-(1-methylheptyl)-amine, di-(2-methylheptyl)-amine, di-(3-methylheptyl)-amine, di-(4-methylheptyl)-amine, di-(5-methylheptyl)-amine, di-(6-hexyl)-amine, di-(3-ethylhexyl)amine, di-(4-ethylhexyl)-amine, methylethylamine, ethylbutylamine, dilaurylamine, didodecylamine, ditridecylamine, dipalmitylamine, distearylamine and dioleylamine.

Suitable cycloaliphatic secondary amines include the following: dicyclohexylamine, 4,4'-dimethyldicyclohexylamine, 3,3'-dimethyldicyclohexylamine, 2,2'-dimethyldicyclohexylamine; N-methylcyclohexylamine, N-ethylcyclohexylamine, N-propylcyclohexylamine, N-isopropyl-cyclohexylamine, N-butyl-cyclohexylamine, N-sec.-butylcyclohexylamine, N-tert.-butylcyclohexylamine, N-pentycyclohexylamine, N-(1-methylbutyl)-cyclohexylamine, N-(2-methylbutyl)-cyclohexylamine, N-(3-methyl-butyl)-cyclohexylamine, N-(1,1-dimethylpropyl)-cyclohexylamine, N-(2,2-dimethylpropyl)-cyclohexylamine, N-(1,2-dimethylpropyl)-cyclohexylamine, N-hexylcyclohexylamine, N-(1-methylpropyl)-cyclohexylamine, N-(2-methylpentyl)-cyclohexylamine, N-(3-methyl-pentyl)-cyclohexylamine, N-(4-methylpentyl)-cyclohexylamine, N-(1,1-dimethylbutyl)-cyclohexylamine, N-(2,2-dimethylbutyl)cyclohexylamine, N-(3,3-dimethylbutyl)-cyclohexylamine, N-(2,3-dimethylbutyl)-cyclohexylamine, N-(1-ethylbutyl)-cyclohexylamine, N-(2-ethylbutyl)-cyclohexylamine, N-heptylcyclohexylamine, N-(1-methylhexyl)-cyclohexylamine, N-(2-methylhexyl)-cyclohexylamine, N-(3-methylhexyl)-cyclohexylamine, N-(1-ethylpentyl)-cyclohexylamine, N-(2-ethylpentyl)-cyclohexylamine, N-3-ethylpentyl)-cyclohexylamine, N-octylcyclohexylamine, N-(1-methylheptyl)-cyclohexylamine, N-(2-methylheptyl)-cyclohexylamine, N-(3-methylheptyl)-cyclohexylamine, N-(4-methylpentyl)-cyclohexylamine, N-(5-methylheptyl)-cyclohexylamine, N-(6-methylheptyl)-cyclohexylamine, N-(1-ethylhexyl)-cyclohexylamine, N-(2-ethylhexyl)-cyclohexylamine, N-(3-ethylhexyl)-cyclohexylamine, N-(4-ethylhexyl)cyclohexylamine, dicyclopentylamine, N-methylcyclopentylamine, N-ethylcyclohexyl-amine, N-methylcyclobutylamine, N-methylcycloheptylamine and N-ethylcycloheptylamine.

Suitable araliphatic secondary amines are the listed aliphatic and cycloaliphatic amines having one or several of their carbon chain hydrogen atoms substituted by aryl radicals, as for example the following: dibenzylamine, di-(2-phenylethyl)-amine, di-(2-phenylpropyl)-amine, di-(3-phenylpropyl)-amine, N-methylbenzylamine, N-ethylbenzylamine, and N-propylbenzylamine.

As mentioned hereinabove, the substituents of the secondary amine may be identical or different. They may also be connected with one another via a common bridge bond. Examples of such cyclic amines are piperidine, pyrrolidine and derivatives, as well as other nitrogen heterocycles.

In the process pursuant to the invention, the oxidant used in oxygen, or a gas containing oxygen such as air. Non-aqueous solvents suitable for the present process include aromatic hydrocarbons such as benzene, toluene, xylene, or nitrobenzene; aliphatic esters; alkyl ether; lower alcohols, such as the $C_1$–$C_4$ alcohols including methanol, ethanol, isopropanol, n-propanol, t-butanol, and amyl alcohol; chlorinated hydrocarbons, such as dichloromethane, chloroform, dichloroethane, trichloroethane; and aprotic solvents such as dimethyl formamide, acetonitrile, dimethyl acetamide, dimethyl sulfoxide, and hexamethylphosphoric triamide. Suitable aqueous solvent include water/alcohol mixtures. High yields and selectivities may be obtained in pure water, but in general the reaction rate in water is slower than in the above-mentioned non-aqueous solvents. Preferred solvents include aromatic hydrocarbons, low alcohols, and alcohol/water mixtures.

The process pursuant to the invention is carried out at temperatures in the range from 0° to 200° C., preferably at 20° to 90° C. temperatures above 90° C. are less preferable for economic and safety reasons. Preferably, the process pursuant to the invention is carried out at oxygen pressures, or at partial oxygen pressures of at least 0.1 bar. Expectably, the reaction rate increases with rising oxygen pressure.

In principle, the present process may be carried out according to three methods of synthesis. In the first process variant, a secondary amine and carbon disulfide at a molar ratio of 1.0 to 1.2:1, in the presence of oxygen or a gas containing oxygen and the metalliferous catalyst can be reacted directly to form the corresponding thiuram disulfide. In the second variant, the carbon disulfide and the secondary amine at a molar ratio of 0.9 to 1.1:2.0 to 2.1 may be reacted. Thereafter, the resulting reaction mixture is reacted with approximately 1.0–1.2 moles of carbon disulfide per mole of carbon disulfide reacted in the first step in the presence of the metalliferous catalyst and oxygen or a gas containing oxygen. In the third process variant, the dithiocarbamate formed by the reaction of the secondary amine and carbon difulfide is isolated as an intermediate product, after which this dithiocarbamate is reacted with 1.0–1.2 moles of carbon disulfide per mole of carbon disulfide reacted in the first step, in the presence of oxygen or a oxygen-containing gas and the metalliferous catalyst. The duration of the reaction depends upon the process conditions, and lies within a range from a few minutes to several hours. Under optimal temperature and oxygen pressure conditions it amounts to a few minutes.

The process pursuant to the invention can be carried out in a simple manner, as by forcing oxygen or the gas containing oxygen onto the reaction solution under the indicated pressure and temperature conditions, or by conducting it into or through the reaction solution. This reaction solution consists of solvent, secondary amine, catalyst and carbon disulfide, or of solvent, catalyst and dithiocarbamate, or of the reaction mixture obtained in the reaction of secondary amine and carbon disulfide in the solvent, and the catalyst. In most cases, as for example with tetramethyl thiuram disulfide, the end product will immediately precipitate out of the reaction mixture and can be filtered off. In other cases, one obtains the desired end product when the reaction mixture is cooled or concentrated. Liquid products may be separated by means of distillation or extraction.

In an industrial-scale process pursuant to the invention it is advantageous to circulate the mother liquor so as to preclude the need for steady addition of fresh metalliferous catalyst. It is, for example, possible to run more than ten reaction cycles with a constant high yield and without loss in catalyst activity. Practically quantitiative yields and selectivities can be obtained in the process pursuant to the invention. The resulting products are very pure and generally need no further purification. Compared with the known two-stage process in which the dithiocarbamate is synthesized first, the present single-stage process is advantageous in that it is economical and in that no auxiliary materials are used. In contrast to the single-stage process known from German published application No. 11 65 011, the present process utilizes simple and inexpensive catalysts. A further advantage is that in the industrial-scale process pursuant to the invention, soluble, recirculable catalysts which do not lose their activity and which result in practically quantitative yields are used.

The thiuram disulfides to be prepared pursuant to the invention are in particular used as fungicides and as vulcanization accelerators for artificial and natural rubber. Several embodiments of the invention are disclosed hereinbelow:

EXAMPLE 1

This example illustrates the first of the above three procedures. 13.5 g (0.3 mol) of dimethylamine and 43.5 mg of Ce(III)nitrate.6H$_2$O (0.1×10$^{-3}$ mol) were dissolved in 100 g of isopropanol in a 500 ml glass autoclave equipped with a jacket to permit circulation of a heating liquid, a thermometer, a pressure measuring device and a stirrer. 25.1 g of CS$_2$ (0.33 mol) were added to this solution with heating. The resulting light yellow, clear solution was heated to 50° C. while stirring vigorously and 1.7 bar of oxygen was forced in. A strong absorption of oxygen was observed at once during this exothermal reaction, and the reaction solution became turbid due to the separation of tetramethyl thiuram disulfide. No additional oxygen was absorbed after 15 minutes, as the dimethylamine had been completely reacted. The white crystalline precipitate was filtered off, washed with isopropanol, and dried. 35.7 g of a product were obtained, which, upon elementary analysis, IR, $^1$H-NMR, and MS corresponded to tetramethyl thiuram disulfide (TMTD) at a chromatographically proven purity of 100% (FP=156° C.). According to NMR analysis, the mother liquor contained another 0.24 g of TMTD. Thus, the total yield of TMTD was 35.94 g, corresponding to 99.8% of theoretical referred to dimethylamine. The selectivity was also 99.8%.

EXAMPLE 2

This example illustrates the second of the above three procedures. A solution of 13.5 g (0.3 mol) of dimethylamine and 100 g of methanol in a glass reaction vessel equipped with reflux cooler and stirring device was reacted while being cooled with 12.4 g (0.16 mol) of carbon disulfide. The solution obtained in this exothermic reaction was transferred to a 500 ml glass autoclave, mixed with 24.4 mg (0.1×10$^{-3}$ mol) of Mn(CH$_3$COO)$_2$.4H$_2$O, heated to 50° C. and stirred vigorously with 1.7 bar of oxygen being applied concurrently. 11.4 g (0.15 mol) of carbon disulfide were added during the reaction at a rate corresponding to that at which dimethylamine was set free. A rapid absorption of oxygen was noted at once and the solution became turbid due to the separation of tetramethyl thiuram disulfide. The addition of carbon disulfide was ceased after 44 minutes and the reaction came to an end after 47 minutes as evidenced by an end to the further absorption of oxygen and a color change from violet-brown to pale yellow. The total yield of TMTD was 35.8 g, corresponding to 99.4% of theoretical.

EXAMPLE 3

This example illustrates the third of the above three procedures. 30.4 g (0.4 mol) of carbon disulfide were, with cooling, added to a solution of 36 g (0.8 mol) dimethylamine in 100 g of methanol. The resulting white precipitate was filtered off, washed with cold methanol, and dired. It consisted of pure dimethylammonium and dimethyldithiocarbamate.

24.9 g (0.15 mol) of this substance were dissolved in 100 g of methanol in the reaction equipment described in Example 1, and 12.2 g (0.16 mol) of carbon disulfide added thereto. This solution was mixed with 24.4 mg (0.1×10$^{-3}$ mol) of Mn(CH$_3$COO)$_2$.4H$_2$O, heated to 50° C. and stirred vigorously, while 1.7 bar of oxygen was applied. A rapid absorption of oxygen was recorded at once, and the solution became turbid due to the separation of tetramethyl thiuram disulfide. After 52 minutes the reaction had come to an end as evidenced by no further absorption of oxygen and a color change from violet-brown to pale yellow. The white, finely crystalline precipitate was filtered off, washed, and dried, and proved to be 35.5 g of tetramethyl thiuram disulfide. The mother liquor contained another 0.32 g of this substance, so that the total yield of tetramethyl thiuram disulfide was 35.82 g, corresponding to 99.5% of theoretical.

EXAMPLES 4

The work was carried out as in Example 3, but now the rate of addition of carbon disulfide corresponded to the rate at which dimethylamine was released during the reaction. No further carbon disulfide was added after 46 minutes and the reaction had ended after 49 minutes. This method yielded a total of 35.85 g of tetramethyl thiuram disulfide, corresponding to 99.6% of theoretical.

EXAMPLE 5

The work was performed as in Example 1, but only 8.7 mg ($0.02 \times 10^{-3}$ mol) of cerium(III) nitrate were used. The absorption of oxygen came to an end after 75 minutes. The total yield of TMTD was 35.89 g, corresponding to 99.7% of theoretical.

EXAMPLE 6 AND 7

These examples were performed in a manner similar to that of Example 2, but different cerium compounds were used as catalysts. The results of these experiments are compiled in the following table:

| Example No. | Catalyst ($0.02 \times 10^{-3}$ mol) | Reaction Time (minutes) | Yield of TMTD (% of theoretical) |
|---|---|---|---|
| 6 | $Ce(NH_4)_2(NO_3)_6$ | 78 | 99.2 |
| 7 | $(CH_3)_2NCS_2)_3Ce$ | 72 | 99.5 |

EXAMPLES 8 AND 9

In the following examples, additional heavy metal compounds were used as catalysts. 13.5 g (0.3 mol) of dimethylamine and 23.6 g (0.31 mol) of carbon disulfide in 100 g of methanol were reacted with oxygen in the manner described in Example 1. Each time, the oxygen pressure was 5 bar and the reaction temperature 50° C. The amount and kind of catalyst used, the reaction time, and the yield of tetramethyl thiuram disulfide are compiled in the following table:

| Catalyst | Catalyst Quantity $10^{-3}$ mol | Reaction Time hours | Yield of TMTD (% of theoretical) |
|---|---|---|---|
| $VOSO_4.5H_2O$ | 0.2 | 4 | 97.2 |
| $MoO_2(acac)_2$ | 0.4 | 9 | 96.4 |

EXAMPLE 10

13.5 g (0.3 mol) of dimethylamine and 24.4 mg ($0.1 \times 10^{-3}$ mol) of $Mn(CH_3COO)_2.4H_2O$ were dissolved in 100 g of isopropanol in the reaction equipment described in Example 1. 22.8 g (0.3 mol) of carbon disulfide were added to this solution. The resulting clear, dark brown solution was heated to 50° C., stirred vigorously, and subjected to 1.7 bar of oxygen. Under these conditions, the reaction came to an end after 90 minutes. TMTD was obtained with a yield of 98.6%.

EXAMPLE 11

In the reaction equipment described in Example 1, 21.9 g (0.3 mol) of diethylamine were dissolved in a solution of 24.4 mg ($0.1 \times 10^{-3}$ mol) of $Mn(CH_3COO)_2.4H_2O$ in 100 g of isopropanol. 23.6 g (0.31 mol) of carbon disulfide were added to this solution with heating. The resulting clear, dark brown solution was quickly heated to 50° C., stirred vigorously, and 1.7 bar of oxygen was applied thereto. An absorption of oxygen was noted immediately; the reaction ceased after 75 minutes, as evidenced by no further absorption of oxygen and the changing of the solution to a pale color. The white, crystalline precipitate that was deposited when the reaction solution cooled was filtered off, washed with isopropanol, and dried. 41.8 g of a product was obtained in this manner, which upon analysis corresponded to tetraethyl thiuram disulfide, and which, according to $^1HNMR$ and chromatographic analysis, had a purity of 100% (FP=72° C.). The mother liquor contained another 1.8 g of tetraethyl thiuram disulfide, which could be isolated in pure form by concentrating the solution and washing the residue with isopropanol. Thus, the total yield of tetraethyl thiuram disulfide amounted to 43.6 g, corresponding to a yield of 98.2% of theoretical.

EXAMPLES 12 TO 18

The work was carried out as in Example 6, but solvents other than isopropanol were used. The results of these experiments are compiled in the following table. "TETD" is tetraethyl thiuram disulfide.

| Example No. | Solvent | Reaction Time (minutes) | Yield of TETD (% of theoretical) |
|---|---|---|---|
| 12 | methanol | 55 | 97.5 |
| 13 | ethanol | 85 | 98.2 |
| 14 | n-propanol | 85 | 98.0 |
| 15 | t-butanol | 90 | 98.9 |
| 16 | t-amyl alcohol | 100 | 97.8 |
| 17 | toluene | 100 | 98.4 |
| 18 | water | 220 | 93.6 |

EXAMPLES 19 TO 23

The work was carried out as in Example 6, except that manganese or manganese-containing compounds were used as catalysts. The results of these experiments are set forth below.

| Example No. | Catalyst ($0.1 \times 10^{-3}$ mol) | Reaction Time (minutes) | Yield of TMTD (% of theoretical) |
|---|---|---|---|
| 19 | Mn powder | 120 | 98.2 |
| 20 | $MnSO_4$ | 200 | 98.5 |
| 21 | $MnO_2$ | 140 | 97.9 |
| 22 | Mn | 290 | 97.3 |
| 23 | $Mn((C_2H_5)_2NCS_2)_2$ | 70 | 98.6 |

EXAMPLE 24

The work was carried out as in Example 6, but 8.6 mg ($0.02 \times 10^{-3}$ mol) of cerium(III) nitrate were used instead of manganese(II)-acetate. The reaction came to an end after 80 minutes. 41.9 grams of tetraethyl thiuram disulfide precipitated during cooling, and was filtered out, washed and dried. The mother liquor contained another 1.7 g of the product. Thus, the total yield of tetraethyl thiuram disulfide was 43.6 g, corresponding to 97.7% of theoretical.

EXAMPLE 25

The work was carried out as in Example 6, but 43.5 mg ($0.1 \times 10^{-3}$ mol) of cerium(III) nitrate were used, and the reaction was performed at room temperature and at an oxygen pressure of 1.7 bar. Oxygen absorption was observed immediately and after a short time the solution became turbid due to the separation of tetraethyl thiuram disulfide. The reaction ceased after 75 minutes. The white precipitate that was filtered off, washed and dried was 41.8 g of tetraethyl thiuram disulfide. The mother liquor contained another 1.8 g of this product. Thus, the total yield of tetraethyl thiuram disulfide was 43.6 g, corresponding to 98.2% of the theory.

EXAMPLES 26 TO 29

In the reaction equipment described in Example 1, 13.5 g (0.3 mol) of dimethylamine, together with a metal catalyst (see table) were dissolved in 100 g of alcohol. 23.6 g (0.31 mol) of carbon disulfide were added thereto, and the reaction mixture oxidized with oxygen, varying the reaction temperature and the oxygen pressure.

after 75 minutes. 35.1 g of a white, crystalline product were obtained by concentrating and cooling the reaction solution. Upon analysis, the product was found to correspond to tetra-n-propyl thiuram disulfide (yield=99.2% of theoretical, FP=60° C.).

EXAMPLE 32

30.3 g (0.3 mol) of diisopropylamine, 23.6 g (0.31 mol) of carbon disulfide, and 24.4 mg ($0.1 \times 10^{-3}$ mol) of $Mn(CH_3COO)_2.4H_2O$ in 100 g of isopropanol were reacted in the manner described in Example 1. The oxygen pressure was 1.8 bar, the reaction temperature 50° C., and the duration of the reaction 60 minutes. The white precipitate (36.4 g) formed during cooling of the reaction solution consisted of tetraisopropyl thiuram disulfide, as determined by physical and chemical analysis. Another 11.2 g of this substance precipitated upon concentration of the mother liquor so that the total yield of tetraisopropyl thiuram disulfide was 47.6 g, corresponding to 90.2% of theoretical (FP=112° C.).

EXAMPLE 33

In order to prepare tetra-n-butyl thiuram disulfide, 25.85 g (0.2 mol) of di-n-butylamine, 16.0 g (0.21 mol) of carbon disulfide, and 24.4 mg ($0.1 \times 10^{-3}$ mol) of $Mn(CH_3COO)_2.4H_2O$, in 100 g of isopropanol were reacted with oxygen in the manner described in Example 1. The reaction temperature was 50° C., the oxygen

| Example No. | Catalyst ($10^{-3}$ mol) | Reaction temp. (°C.) | Solvent (alcohol) | $O_2$ press. (bar) | Reaction Time (min.) | DMA convers. (%) | TMTD Yield % of theor. |
|---|---|---|---|---|---|---|---|
| 26 | $Cu(OAc)_2$ (0.1) | 25 | isopropanol | 1.7 | 200 | 54.2 | 53.4 |
| 27 | $Mn(OAc)_2$ (0.1) | 85 | methanol | 5.0 | 9 | 100 | 98.8 |
| 28 | $Ce(NO_3)_3$ (0.5) | 50 | isopropanol | air, norm. pressure | 190 | 92.3 | 91.0 |
| 29 | $Cu(OAc)_2$ (0.1) | 50 | isopropanol | 10 | 50 | 99.5 | 98.6 |

These examples demonstrate that the process is operable within a wide range of temperatures and pressures and with consistently high selectivity.

EXAMPLE 30

In the reaction equipment described in Example 1, 25.5 g (0.3 mol) of piperidine and 24.4 mg ($0.1 \times 10^{-3}$ mol) of $Mn(CH_3COO)_2.4H_2O$ were dissolved in 100 g of isopropanol. 23.6 g (0.31 mol) of carbon disulfide were added to this solution. The resulting clear, dark solution was heated to 50° C., stirred vigorously, and oxygen at 1.7 bar was applied thereto. After a short time, the solution became turbid due to the separation of the product. The reaction ceased after 60 minutes, and the white precipitate that was separated, washed and dried proved upon analysis to be 46.8 g of dipentamethylene thiuram disulfide (FP=132° C.). Another 0.4 g of this product were contained in the mother liquor. Thus, the total yield of dipentamethylene thiuram disulfide amounted to 47.2 g, corresponding to 98.3% of theoretical.

EXAMPLE 31

20.2 g (0.2 mol) of di-n-propylamine, 24.4 mg ($0.1 \times 10^{-3}$ mol) of $Mn(CH_3COO)_2.4H_2O$ and 100 g of isopropanol were charged to the reaction equipment described in Example 1. 16.0 g (0.21 mol) of carbon disulfide were added thereto, and the resulting solution was heated to 50° C., treated with oxygen at a pressure of 1.7 bar, and stirred vigorously. An immediate absorption of oxygen was observed and the reaction ceased pressure 1.8 bar, and the reaction time required for complete conversion 105 minutes. Processing by means of distillation resulted in retrieval of 40.2 g of the product in the form of an oil. The yield was 98.5% of theoretical.

EXAMPLE 34

25.85 g (0.2 mol) of di-i-butylamine, 16.0 g (0.21 mol) of carbon disulfide, and 24.4 mg ($0.1 \times 10^{-3}$ mol) of $Mn(CH_3COO)_2.4H_2O$, in 100 g of isopropanol were reacted with oxygen in the manner described in Example 1. The reaction temperature was 50° C., the oxygen pressure 1.8 bar, and the duration of the reaction 90 minutes. The white precipitate obtained upon concentration of the reaction solution consisted of tetra-i-butyl thiuram disulfide, as determined by physical and chemical analysis. The yield was 36.8 g. corresponding to 90.2% of theoretical (FP=71° C.).

EXAMPLE 35

Ditetramethylene thiuram disulfide was prepared in the manner described in Example 1, from 14.2 g (0.2 mole) pyrrolidine and 16.0 g (0.21 mole) of carbon disulfide, in the presence of 24.4 mg ($0.1 \times 10^{-3}$ mole) of $Mn(CH_3COO)_2.4H_2O$ and 100 g of isopropanol. The reaction temperature was 50° C., the oxygen pressure 1.8 bar, and the reaction time 30 minutes. The white precipitate formed in the course of the reaction was filtered off, washed, and dried and consisted of pure ditetramethylene thiuram disulfide (analytical determination by means of elementary analysis, $^1$H-NMR, IR, MS). The yield was 27.5 g, corresponding to 94.2% of theoretical (FP=140° C.).

EXAMPLE 36

22.6 g (0.2 mole) of N-methylcyclohexylamine and 16.0 g (0.21 mole) of carbon disulfide in 100 g of isopropanol were reacted in the presence of 24.4 mg ($0.1 \times 10^{-3}$ mol) of Mn(CH$_3$COO)$_2$.4H$_2$O in the manner described in Example 1. The oxygen pressure was 1.8 bar, the reaction temperature 50° C., and the duration of the reaction up to complete conversion was 85 minutes. The white precipitate, which was already formed during the reaction, was filtered off, washed, and dried, and was characterized as pure N,N'-dimethyl-N,N'-dicyclohexyl thiuram disulfide (31.3 g) by means of chemical and physical analysis. Another 5.6 g of this substance precipitated out upon concentration of the mother liquor, so that the total yield was 36.9 g, corresponding to 98.1% of theoretical (FP=112° C.).

EXAMPLE 37

39.5 g (0.2 mole) of dibenzylamine and 16.0 g (0.21 mole) of carbon disulfide, in 100 g of methanol were reacted with 24.4 mg ($0.1 \times 10^{-3}$ mole) of Mn(CH$_3$COO)$_2$.4H$_2$O in the manner described in Example 1. The oxygen pressure was 1.8 bar, the reaction temperature 50° C., and the time of reaction was three hours. The white precipitate formed during the reaction was determined by physical and chemical analysis to be tetrabenzyl thiuram disulfide (FP=136° C.). The yield was 52.1 g, corresponding to 95.6% of theoretical.

What is claimed is:

1. A process for the preparation of thiuram disulfides substituted with one or more of the group consisting of aliphatic, araliphatic, and cycloaliphatic hydrocarbon radicals, said process comprising reacting a suitably substituted secondary amine with carbon disulfide in a solvent and in the presence of oxygen or an oxygen-containing gas and a metalliferous catalyst, said secondary amine having a pK$_a$ value of $\geq 8$, said carbon disulfide and the secondary amine being reacted in a molar ratio of 1.0 to 1.2:1, and said process being maintained at a reaction temperature between 0° and 200° C., said metalliferous catalyst being selected from the group consisting of elemental copper, copper(I) chloride, copper(I) bromide, copper(I) iodide, addition compounds of copper(I) halides with carbon monoxide, alkali chlorocuprates, complex ammoniacates of copper(I) cyanide, potassium tricyanocuprate(I), double salts with copper(I) thiocyanate, copper(I) acetate, copper(I) sulfide, complex double sulfides of copper(I) sulfide, alkali polysulfides, copper(I) chloride, copper(II) bromide, copper(II) sulfide, copper(II) nitrite, copper(II) thiocyanate, copper(II) cyanide, copper(II) acetate, copper dithiocarbamate, complex ammoniacates of copper(II) salts, copper(I) oxide, metallic cerium, cerium dioxide, cerium(III) chloride, cerium chloride, cerium chloro-complex salts, cerium nitrate, cerium nitrato salts, cerium sulfate, cerium carbonate, cerium oxalate, cerium sulfides, vanadium oxide, vanadium chloride, vanadium sulfates, molybdenum oxides, molybdenum chloride, molybdenum sulfide, molybdenum fluoride, molybdates, and molybdenum complex acido salts, manganese powder, manganese dioxide, potassium permanganate, manganese acetate and manganese dithiocarbamates.

2. The process as set forth in claim 1, wherein 0.01 to 5 mmol of said metalliferous catalyst is used per mole of secondary amine.

3. The process as set forth in claim 1 or 2, wherein said solvent is selected from one or more of the group including an aromatic hydrocarbon, a C$_1$-C$_4$ alcohol, and water.

4. A process for the preparation of thiuram disulfides substituted with one or more of the group consisting of aliphatic, araliphatic, and cycloaliphatic hydrocarbon radicals, said process comprising a first reaction in which a suitably substituted secondary amine is reacted with carbon disulfide in a molar ratio of 0.9 to 1.1:2.0 to 2.2 and in a solvent, said secondary amine having a pK$_a$ value of $\geq 8$, and then adding thereto 1.0 to 1.2 moles of carbon disulfide per mole of carbon disulfide added in said first reaction in the presence of a metalliferous catalyst and oxygen or an oxygen-containing gas, said process being maintained at a reaction temperature between 0° and 200° C., said metalliferous catalyst being selected from the group consisting of elemental copper, copper(I) chloride, copper(I) bromide, copper(I) iodide, addition compounds of copper(I) halides with carbon monoxide, alkali chlorocuprates, addition compounds of copper(I) halides with carbon monoxide, alkali chlorocuprates, complex ammoniacates of copper(I) cyanide, potassium tricyanocuprate(I), double salts with copper(I) thiocyanate, copper(I) acetate, copper(I) sulfide, complex double sulfides of copper(I) sulfide, alkali polysulfides, copper(II) chloride, copper(II) bromide, copper(II) sulfide, copper(II) nitrite, copper(II) thiocyanate, copper(II) cyanide, copper(II) acetate, copper dithiocarbamate, complex ammoniacates of copper(II) salts, copper(I) oxide, metallic cerium, cerium dioxide, cerium(III) chloride, cerium chloride, cerium chloro-complex salts, cerium nitrate, cerium nitrato salts, cerium sulfate, cerium carbonate, cerium oxalate, cerium sulfides, vanadium oxide, vanadium chloride, vanadium sulfates, molybdenum oxides, molybdenum chloride, molybdenum sulfide and molybdenum fluoride, molybdates, and molybdenum complex acido salts, manganese powder, manganese dioxide, potassium permanaganate, manganese acetate and manganese dithiocarbamates.

5. The process as set forth in claim 4, wherein 0.01 to 5 mmol of said metalliferous catalyst is used per mole of secondary amine.

6. The process as set forth in claim 4 or 5, wherein said solvent is selected from one or more of the group including an aromatic hydrocarbon, a C$_1$-C$_4$ alcohol, and water.

7. A process for the preparation of thiuram disulfides substituted with one or more of the group consisting of aliphatic, araliphatic, and cycloaliphatic hydrocarbon radicals, said process comprising reacting carbon disulfide and a suitably substituted secondary amine having a pK$_a$ value of $\geq 8$ in a molar ratio of 0.9 to 1.1:2.0 to 2.2 to form a dithiocarbamate, isolating said dithiocarbamate, and reacting said dithiocarbamate with carbon disulfide in a molar ratio of 1.0:1.0 to 1.2 in the presence of oxygen or an oxygen-containing gas and a metalliferous catalyst, and said process being maintained at a reaction temperature between 0° and 200° C., said metalliferous catalyst being selected from the group consisting of elemental copper, copper(I) chloride, copper(I) bromide, copper(I) iodide, addition compounds of copper(I) halides with carbon monoxide, alkali chlorocuprates, complex ammoniacates of copper(I) cyanide, potassium tricyanocuprate(I), double salts with copper(I) thiocyanate, copper(I) acetate, copper(I) sulfide, complex double sulfides of copper(I) sulfide, alkali polysulfides, copper(II) chloride, copper(II) bromide, copper(II) sulfide, copper(II) nitrite, copper(II) thiocyanate, copper(II) cyanide, copper(II) acetate, copper dithiocarbamate, complex ammoniacates of copper(II) salts, copper(I) oxide, metallic cerium, cerium dioxide, cerium (III) chloride, cerium chloride, cerium chlorocomplex salts, cerium nitrate, cerium nitrato salts, cerium sulfate, cerium carbonate, cerium oxalate, cerium sulfides, vanadium oxide, vanadium chloride, vanadium sulfates, molybdenum oxides, molybdenum chloride, molybdenum sulfide, molybdenum fluoride, molybdates, and molybdenum complex acido salts, manganese powder, manganese dioxide, potassium permanganate, manganese acetate and manganese dithiocarbamates.

8. The process as set forth in claim 7 wherein 0.01 to 5 mmol of said metalliferous catalyst is used per mole of dithiocarbamate.

9. The process as set forth in claim 7 or 8, wherein said solvent is selected from one or more of the group including an aromatic hydrocarbon, a $C_1$–$C_4$ alcohol, and water.

* * * * *